United States Patent [19]

Warriner

[11] Patent Number: Plant 6,612

[45] Date of Patent: Feb. 14, 1989

[54] ROSE PLANT JACMEY

[75] Inventor: William A. Warriner, Tustin, Calif.

[73] Assignee: Jackson & Perkins Company, Medford, Oreg.

[21] Appl. No.: 69,692

[22] Filed: Jul. 1, 1987

[51] Int. Cl.[4] ..... A01H 5/00

[52] U.S. Cl. ..... Plt./15

[58] Field of Search ..... Plt./15

*Primary Examiner*—James R. Feyrer

*Attorney, Agent, or Firm*—Majestic, Gallagher, Parsons & Siebert

[57] ABSTRACT

A rose variety of the hybrid tea class is provided having a very high cut flower production, long and exceptionally straight stems, deep yellow buds contrasted with semi-glossy dark green leaves, downward hooking reddish colored thorns, five or seven leaflet leaves, and resistance to infection by powdery mildew.

1 Drawing Sheet

SUMMARY OF THE INVENTION

The present invention relates to a new and distinct variety of rose plant of the hybrid tea class, which was originated by me by crossing the variety Golden Emblem, U.S. Plant Pat. No. 5,121, with an unnamed seedling.

The primary objective of this breeding was to produce a new rose variety of the hybrid tea class suitable for geeenhouse production. This objective was substantially achieved, along with other desirable improvements, as evidenced by the following unique combination of characteristics which are outstanding in the new variety and which distinguish it from its parents as well as from all other varieties of which I am aware. For example, this new rose variety has:

1. Very high production of cut flowers;
2. Long, very straight stems;
3. Dark green, semi-glossy leaves;
4. Deep golden yellow buds;
5. Resistance to powdery mildew;
6. Reddish thorns that hook downward;
7. Five or seven leaflet leaves.

Asexual reproduction of this new variety by budding, as performed at Wasco, Calif., shows that the foregoing characteristics and distinctions come true to form and are established and transmitted through succeeding propagation.

DESCRIPTION OF THE DRAWING

The accompanying illustration shows typical specimens of the vegetative growth and flowers of this new variety in different stages of development, depicted in color as nearly true as it is resonably possible to make the same in a color illustration of this character.

DETAILED DESCRIPTION OF THE INVENTION

The following is a detailed description of my new rose cultivar, which as been denominated "Jacmey". Color terminology is in accordance with The Royal Horticultural Society Colour Chart except where an ordinary dictionary significance for the color is apparent.

Observations of the buds and flowers were made from specimens grown in a greenhouse at Irvine, Calif. in the Winter and Spring.

Flower

The blooming habit is continuous. The bud size is one and one-half inches when the petals start to unfurl. The bud form is long, pointed ovoid. The bud color when sepals first divide is near Yellow 12A; when half brown, the upper side of petals is near Yellow 12B and the lower side of petals is near Yellow 12B. The sepals have a color near Green 138B. The surface texture is covered in very fine hairs. There are three appendaged sepals lightly appendaged, and two unappendaged sepals with hairy edge. The receptacle color is near Green 141B with a funnel shape, medium size and smooth surface. The peduncle is medium to short length, and has a smooth surface. Peduncle color is medium green and the penduncle is stiff and erect.

Bloom

Bloom size is large, with an average open size of four and one-half inches, borne singly. The stems are strong and long. The form when first open is high center. The petals then all curl in quill fashion. Under normal conditions there are thirty-five to forty petals. The upper side of petals is Yellow 12A to 12B, as is the reverse side of the petals. The base of petals has a small, intensely yellow half-moon at the point of attachment to the peduncle with the major color being near Yellow 13A. There are no variegations. The general tonality at the end of the first day shows no change in color. At the end of the third day, there remains no discoloration.

The fragrance is slight to moderate. The petal texture is thick, of a deltoid shape, and the tips are slightly recurved and moderately quilled.

The arrangement is imbricated with few petaloids in the center. The blooms drop off cleanly, and last on the plant for a very long period and as a cut flower for a very long time.

Reproductive Parts

The anthers are medium and many, of yellow color, arranged regularly around the styles and are mixed with a few petaloids. The filaments are yellow, the pollen is gold yellow, the styles are reddish, and the stigmas are greenish white.

Plant

A very vigorous, upright growth of bush form.

Foliage

Medium size, normal in quantity. The new foliage has a reddish cast that rapidly turns green. Normal mid-stem leaves have five or seven leaflets.

The leaflets are of an oval pointed shape, are smooth, and have a serrated edge. The serration is single and small in size. Petiole rachis is reddish when young, then green, and petiole underside is smooth. Stipules are medium and serrated. The foliage is resistant to mildew under normal growing conditions at Irvine, Calif.

Wood

New wood is reddish, with a smooth bark. Old wood is green with a smooth bark.

Prickles

There are an ordinary number of prickles on main canes from the base and on laterals from the main canes. The form is medium and hooked downward. Color when young is red.

Small Prickles

There are no small prickles on the main stalks or on the laterals.

Additional Distinguishing Traits

This novel rose plant produces exceptionally upright straight flowering stems in large numbers.

Parentage

The seed parent was Golden Emblem, U.S. Plant Pat. No. 5,121. The pollen parent was an unnamed seedling.

Classification

Botanical is rosa hybrid. Commercial is hybrid tea.

I claim:

1. A new and distinct variety of rose plant and parts thereof of the hybrid tea class substantially as herein shown and described, characterized particularly as to novelty by a very high cut flower production, long and exceptionally straight stems, deep yellow buds contrasted with semi-glossy dark green leaves, downward hooking reddish colored thorns, five or seven leaflet leaves, and resistance to infection by powdery mildew.

* * * * *

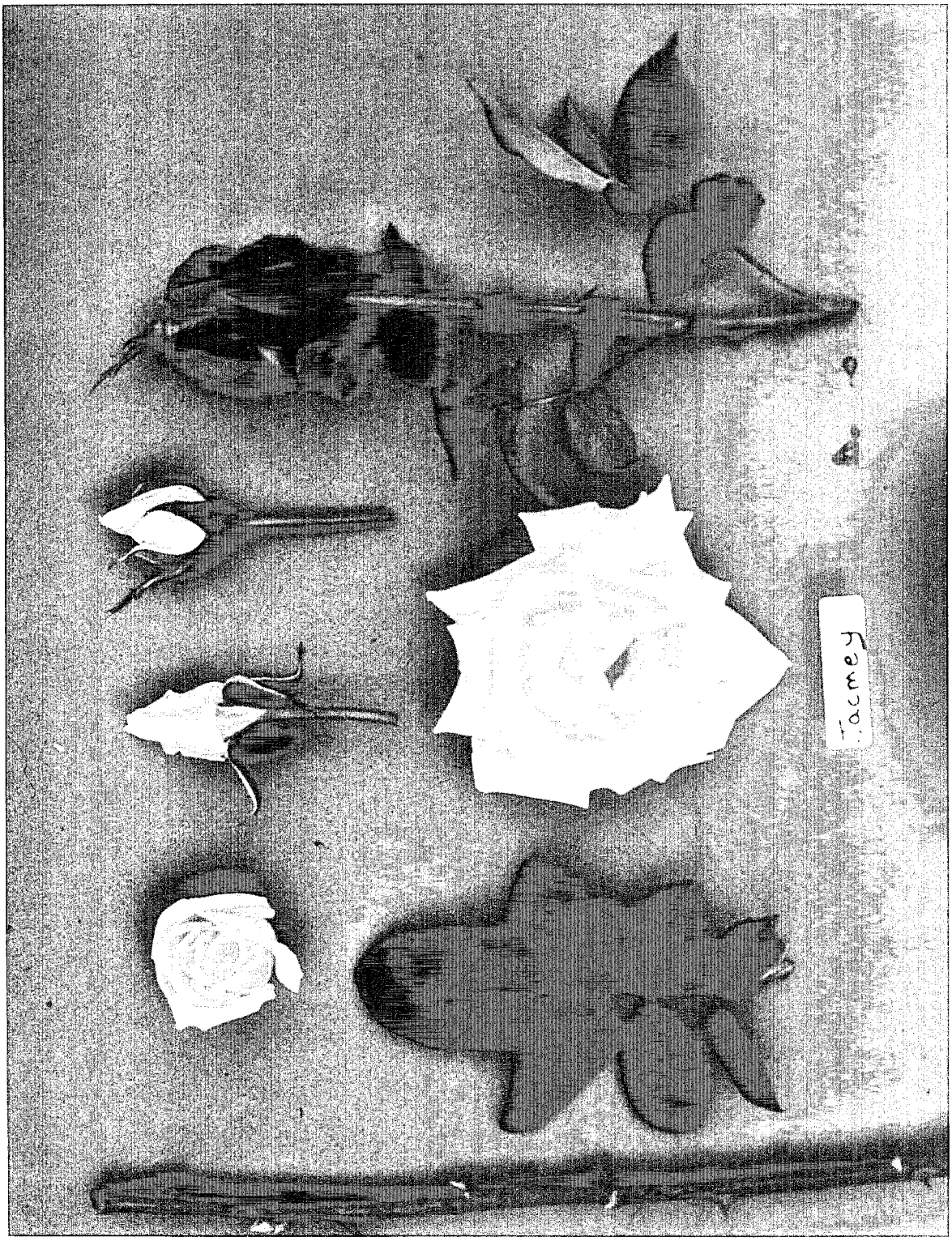
Tacmey